(12) United States Patent
Mulder et al.

(10) Patent No.: US 7,860,277 B2
(45) Date of Patent: Dec. 28, 2010

(54) FOOD PRODUCT CHECKING SYSTEM AND METHOD FOR IDENTIFYING AND GRADING FOOD PRODUCTS

(75) Inventors: Steven C. Mulder, Mechanicsville, VA (US); Calvin G. Gray, Richmond, VA (US); Paul G. Scardino, Layton, UT (US)

(73) Assignee: Bizerba GmbH & Co. KG, Balingen (DE)

( * ) Notice: Subject to any disclaimer, the term of this patent is extended or adjusted under 35 U.S.C. 154(b) by 931 days.

(21) Appl. No.: 11/733,277

(22) Filed: Apr. 10, 2007

(65) Prior Publication Data

US 2008/0253648 A1    Oct. 16, 2008

(51) Int. Cl.
G06K 9/00    (2006.01)
(52) U.S. Cl. .................. 382/110; 382/141
(58) Field of Classification Search .......... 382/110, 382/141
See application file for complete search history.

(56) References Cited

U.S. PATENT DOCUMENTS

| | | | |
|---|---|---|---|
| 5,619,587 A * | 4/1997 | Willoughby et al. | 382/141 |
| 5,793,879 A * | 8/1998 | Benn et al. | 382/110 |
| 6,133,948 A | 10/2000 | Abbott et al. | |
| 6,366,689 B1 * | 4/2002 | Rao et al. | 382/145 |
| 6,414,756 B1 * | 7/2002 | Tsukada | 358/1.9 |
| 6,882,434 B1 * | 4/2005 | Sandberg et al. | 356/601 |
| 2002/0040968 A1 * | 4/2002 | Black et al. | 250/393 |

FOREIGN PATENT DOCUMENTS

| | | |
|---|---|---|
| EP | 0 314 521 | 5/1989 |
| JP | 10-236410 | 9/1989 |
| JP | 11-325836 | 11/1999 |
| JP | 2001-349771 | 12/2001 |
| JP | 2002-2179040 | 6/2002 |
| WO | WO 95/21375 * | 8/1995 |
| WO | WO 98/42196 | 10/1998 |
| WO | WO 02/27281 | 4/2002 |

* cited by examiner

*Primary Examiner*—Bhavesh M Mehta
*Assistant Examiner*—Hadi Akhavannik
(74) *Attorney, Agent, or Firm*—Leydig, Voit & Mayer, Ltd.

(57) ABSTRACT

A food product checking system for at least one of identification and grading of food products packed in a tray is provided, comprising a tray positioning area, an illumination device for illuminating the food product with white light, at least one camera for taking images of the illuminated food product, and an evaluation device for image processing of taken images, wherein the evaluation device is adapted to perform a color analysis of taken images.

37 Claims, 9 Drawing Sheets

FOOD PRODUCT CHECKING SYSTEM AND METHOD FOR IDENTIFYING AND GRADING FOOD PRODUCTS

The present invention is drawn to a food product checking system for at least one of identification and grading of food products packed in a tray.

Further, the invention is related to a method for identifying and grading food products packaged in a tray.

BACKGROUND OF THE INVENTION

It is desirable to have a food product checking system available which can automatically identify and grade food products. Such a system is usable for quality assessment of food products. It is further usable for labeling food products automatically.

WO 02/27281 A1 discloses a weighing system for weighing articles conveyed on a conveyor comprising at least a first and second belt unit, the weighing system comprising a first and second weighing cell supporting the first and second belt unit, respectively, and adapted to provide data of the weight of one or more articles being supported by said belt units, and a control system with detecting means for providing data of at least the location of one or more edges of the article on the conveyor, a processor unit for processing data obtained from said detecting means and weight cells and for determining at least a weight of the article(s) and storing said determined weight.

WO 98/42196 A1 discloses an apparatus for removing the ribs portion from the belly of an animal flank, comprising transport means, image sensing means, means for generating surface profile data characterizing the flank top surface, means for generating ribs thickness data for the ribs, processor means, robot means provided with a cutting means and controller means operable to produce relative movement between the cutting means and the flank according to programmed cut data.

U.S. Pat. No. 6,133,948 A discloses an automated identification system comprising a first classification station which uses two laser sources and video imaging techniques to identify and distinguish between similar items addressed, for example, wooded cabinet doors and drawer fronts.

SUMMARY OF THE INVENTION

In accordance with the present invention, a food product checking system for at least one of identification and grading of food products packed in a tray is provided, comprising a tray positioning area, an illumination device for illuminating the food product with white light, at least one camera for taking images of the illuminated food product, and an evaluation device for image processing of taken images, wherein the evaluation device is adapted to perform the color analysis of taken images.

In accordance with the present invention, the food product (and also the tray) is illuminated by white light. Accordingly, the tray positioning area and thereby the food product and the tray can be illuminated by white light in a broad spectrum. The taken images can be color analyzed in a simple manner. It is simple to achieve a high color resolution and thereby investigate the food product in a definite manner.

The white light contains light of other colors, like red light, green light and blue light. The color analysis can be performed by resolving different colors and using the different colors to determine features of the food product and of the packaging of the food product.

For example, in accordance with the present invention, the contours of the food product can be distinguished from the tray in a simple manner. It is also possible to determine in a simple manner inclusions in a seal.

Also, it is possible to analyze a laser line across the food product and the tray in a simple manner when the corresponding light line has a definite color like green.

In particular, the white light is a superposition of red light, green light and blue light. (Other colored light can be included.) Thus, the color analysis can be performed with regard to red, green and blue. Illustratively, it is, for example, possible to distinguish features of meat food products.

In one embodiment, the illumination device comprises a source for white light. For example, the illumination device comprises one or more broadband light emitting diodes.

It is also possible that the illumination device comprises sources for red, green and blue light. Illustratively, the white light is generated as superposition of the light of different sources.

It is advantageous when a reflection area is provided from which white light is directed towards the tray positioning area. The reflection area is a kind of source for white light. For example, the reflection area is formed by plastic panels reflecting light down onto the tray positioning area. Thus, glare on a cover can be minimized.

In particular, the light of the sources for red, green and blue light is directed towards the reflection area and is in particular reflected towards a reflection area.

It is advantageous when at least one light emitting diode is provided as a light source. Light emitting diodes have comparatively low energy consumption and can be arranged in a compact way. Further, the heat production of light emitting diodes is comparatively low. It is possible that one or more broadband white light emitting diodes are provided or that one or more light emitting diodes for different colors like red, green and blue are provided.

It is advantageous when an enclosure is provided for the tray positioning area. Thus, the food product (and a tray) can be illuminated in a defined way minimizing the influence of disturbance light.

It is expedient for the enclosure to have openings allowing a through put of trays. Thus, for example, the trays can be put through a corresponding vision station via a conveyor.

It is particularly advantageous when, within the vision range of the at least one camera, color reference fields are arranged. These color reference fields, which are, for example, formed by corresponding red, green and blue chips, serve as reference colors. The at least one camera can monitor the light level and color balance. It is possible to adjust automatically the settings of the at least one camera when needed. Accordingly, a high reliability of the system can be reached.

It is advantageous when at least one color reference field for the color white is provided. It is then possible to balance a camera on the corresponding white target of this reference field or reference fields and test for example comparing white versus red in a red plane, white versus green in a green plane and so on.

The color reference fields are arranged advantageously at or close to the tray positioning area. Thus, reference fields are positioned in the vision field of the camera.

It is expedient when the at least one evaluation device is adapted to analyze an image with regard to the positions of the colors red, green and blue. For example, it is possible to discern different color areas in a taken image and thereby analyze the food product with regard to different areas. For example for a meat food product, bone areas, fat areas and lean areas can be distinguished.

Further, it is advantageous when the evaluation device is adapted to identify the contour or shape of the food product in the tray and separate the food product from the tray. Thus, the food product analysis can be restricted to the image of the food product. Further, the contour or shape of a food product is in itself an information useful for identifying the food product. Moreover, the shape information for a tray could be a useful information.

If the system comprises a laser device which is adapted to produce at least one laser generated light line across a tray, further evaluation steps (evaluation modules) can be performed. For example, via the laser line it is possible to determine the height of a tray, the dome height of a film cover and it is possible to check whether intrusions are under a cover and, in particular, under a seal area of the cover. Further, it is possible via analyzing the shape of the laser generated light line across the food product in a corresponding image the food product itself.

It is advantageous when the laser device emits light in an angle (oblique) with regard to a plane perpendicular to the tray positioning area. Thus, the offset between a laser area on a tray extension (tray edge) with regard to a laser generated light area on the tray positioning area can be used to determine the height of the tray. Further, with a laser generated light line on a film cover it is possible to determine a film cover dome height.

It is particularly advantageous for checking of meat food products if the laser device generates green light. The evaluation device then can easily determine the laser light area in an image. For other type of food products other laser light colors might be appropriate.

In particular, the evaluation device is adapted to analyze a laser generated light line with regard to segmentation. The segmentation of the laser light line across a food product can give valuable information with regard to the food product.

It can be provided that at least one of the number of segments, length of segments, length distribution of segments, angle of segments, angle distribution of segments and offset between segments is analyzed. Also, the texture of the food product around a laser generated light line can be analyzed.

Further, at least one of the shape of the food product, shape of areas of the food product, distribution of shape of areas of the food product, size of areas of the food product, distribution of size of areas of the food product can be analyzed by the evaluation device.

With the food product checking system in accordance with the present invention, also trays that are sealed by a see-through lid like a film lid can be analyzed.

For example, the evaluation device evaluates a laser generated light line caused by light reflection on said lid. With this light line compared to a laser generated light area on a tray extension, the dome height of the cover can be determined.

In accordance with the present invention it is possible to determine via the evaluation device the height of the tray by comparing the offset of light reflected from the tray positioning area or an area close to the tray positioning area to the laser generated light line on a tray extension.

Further, it is possible to analyze in accordance with the present invention a tray seal area with regard to inclusions. The tray seal area has, if the tray has a certain color, the same color. If there is a color change in this area, an inclusion must be present.

It can be advantageous when the system in accordance with the present invention comprises a first camera and at least one second camera for scanning a laser generated light area. With a second camera, for example, the sealing can be checked with regard to inclusions. With a second camera, it is for example possible to check the seal area continuously.

The system may comprise a conveyor for transporting trays. Accordingly, a high checking rate can be achieved.

It is advantageous when the evaluation device comprises a data storage for stored product identification data and/or product grading data. Such, the evaluation device can calculate for performed analysis modules numerical values and compare them with known stored data for known food products. Thus, it is possible to identify and grade food products.

Provision can be made for a learning section of the evaluation device. Accordingly, new products can be introduced. A new product can be run through the system and the corresponding data can be taken and, if the food product is found to be unique compared to the stored food products, the corresponding data can be stored.

Further, in accordance with the present invention a method for identifying and grading food products packaged in a tray is provided, which comprises evaluating the shape of the food product in the tray, and analyzing the food product with regard to different areas in the food product, wherein for analyzing the food product multiple analysis modules are performed based on different analysis criteria, each analysis module providing an output, and wherein said outputs are compared to stored food product data.

Thus, food products can be identified and graded in an automatic manner with high reliability.

For example, at least five modules are performed. In one embodiment, ten to fifteen (or more) modules are performed providing a corresponding number of criteria. (The number of criteria can be larger than the number of modules performed.) It is then possible to identify food products and/or grade food products with a top-down method. In a top-down method, non-matching food products are eliminated until matching is reached.

In particular, the outputs are numerical values provided by an evaluation device. The evaluation device has reached these numerical output values in particular by image processing.

For example, the analysis steps comprise a color analysis of the food product and a surface analysis of the food product.

The analysis steps are, in particular, based on optical data. In particular, the optical data are based on imaging data processing of images taken by at least one camera.

DETAILED DESCRIPTION OF THE INVENTION

Figure 1:
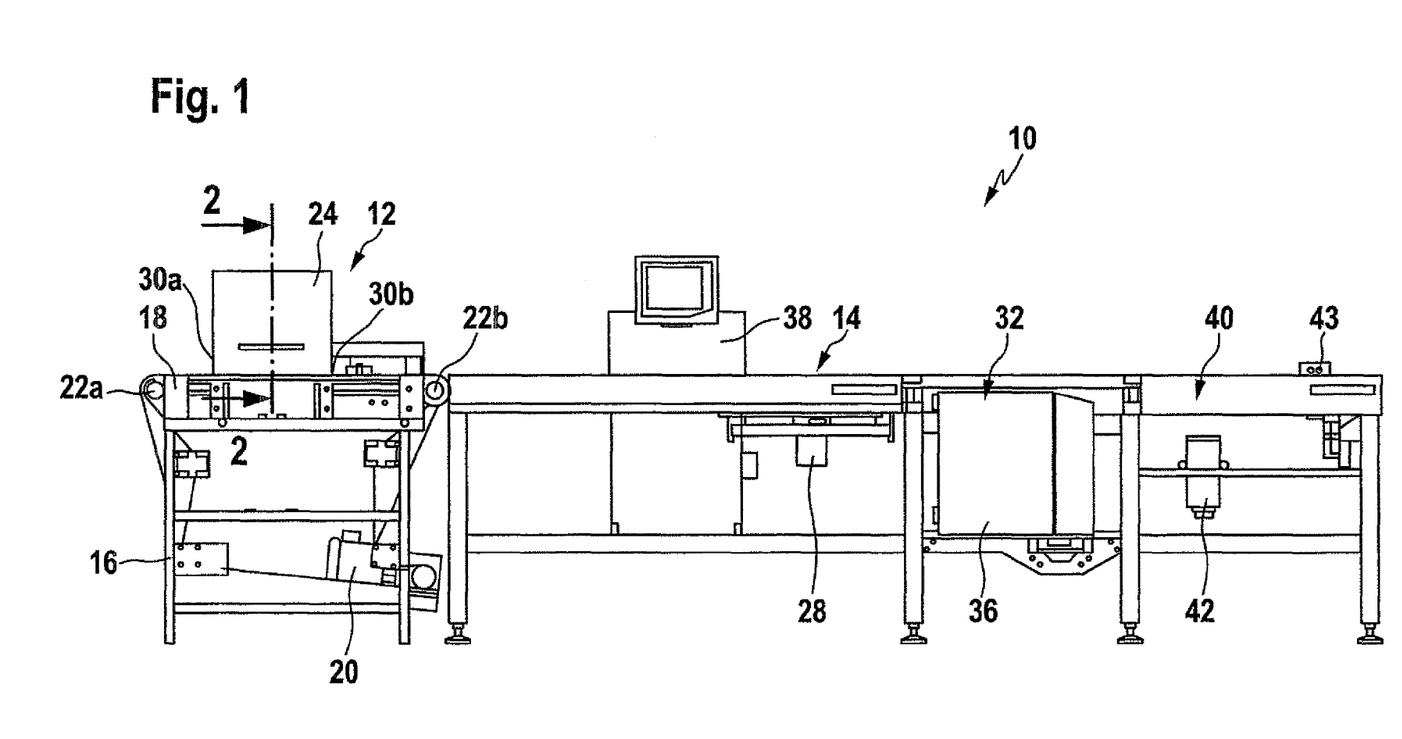
FIG. 1 is a schematic view of an embodiment of a food product checking system in accordance with the present invention.

An embodiment of a food product checking system, which is shown in FIG. 1 and designated as 10, comprises a vision station 12 for performing optical checks on food products. The food product checking system 10 further comprises a weighing station 14 for weighing food products (together with their packages). The vision station 12 and the weighing station 14 can be connected in such a way that during optical inspection of food products a weighing can be performed or they can be separated from each other with the weighing station 14 following sequentially the vision station 12, as shown in FIG. 1.

The vision station 12 comprises a stand 16. On this stand 16, a conveyor belt 18 is guided for transporting food product goods through the vision station 12 (to the weighing station 14). The conveyor belt 18 is driven by a motor 20 that is fixed to the stand 16.

Further, rolls 22*a*, 22*b* are fixed to the stand 16 for guiding the conveyor belt 18.

The vision station 12 comprises an enclosure 24 that is arranged on the stand 16. Within the enclosure 24, food products are illuminated, as described below.

The food products to be checked are packaged in trays as described further below. The vision station 12 comprises a tray positioning area 26 (FIGS. 2, 3) on which trays with food products are to be positioned during examination.

Figure 2:
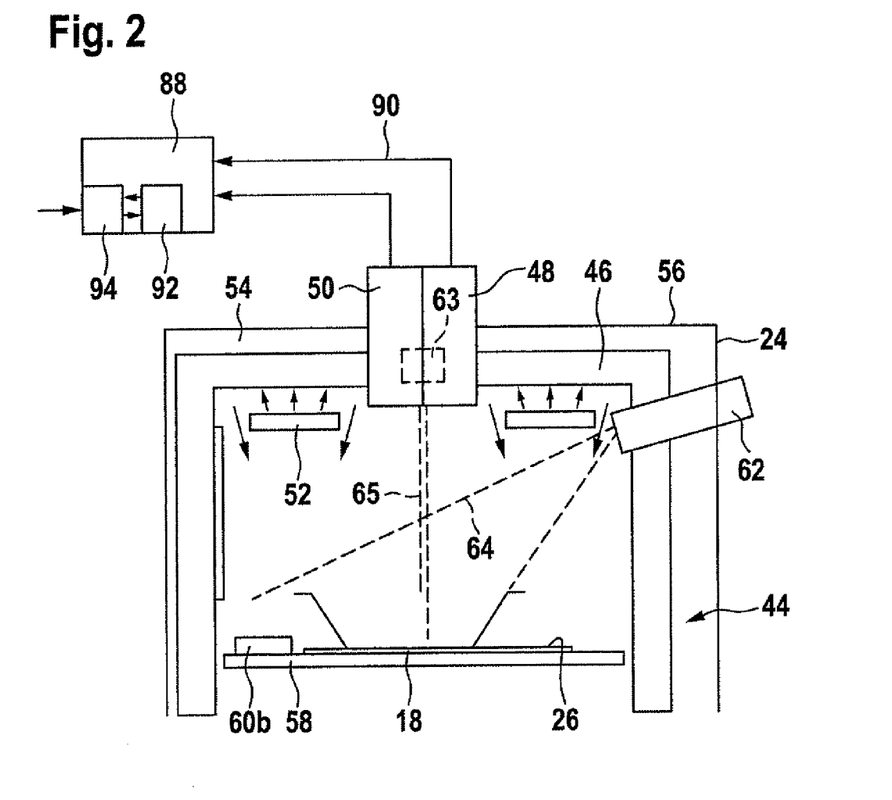
FIG. 2 is a cross section along the line 2-2 of FIG. 1 of a vision station.
Figure 3:
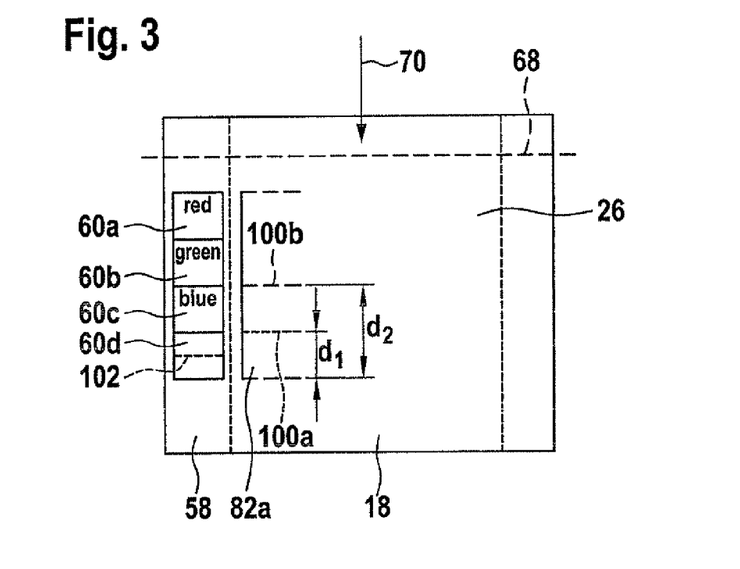
FIG. 3 is a view on a positioning area of the vision station of FIG. 2.

The examination of the food products can be performed with still standing conveyor belt 18 or continuously with moving conveyor belt 18. In the latter case, the tray positioning area 26 can be an area moving together with the conveyor belt 18.

The weighing station 14, which comprises scales 28, is arranged in such a way that the weight of the tray-food product-entity can be measured during or after the optical inspection thereof.

The enclosure 24 has openings 30*a*, 30*b* which are opposite to each other and allow a through-put of food products through the vision station 12.

The food product checking system further comprises a labeling station 32 which is arranged following the weighing station 14. The vision station 12 and the labeling station 32 are connected by a transport station for transporting food products from the vision station 12 to the labeling station 32. At the labeling station 32, the trays with the food product are labeled. The labels, which are for example printed labels, are provided with food product information at the labeling station 32 using the results of the vision station 12 and the weighing station 14. Such, labels can include weight information and can include the sale price which has been calculated using the weight information determined by the weighing station 14 and the product identification information determined via the vision station 12.

The labeling station 32 can, for example, comprise a labeling device 36 that puts labels on food product packages via a stamp or via airflow or via a rotating roller.

The food product checking system 10 further comprises a control device 38 for controlling the vision station 12, the weighing station 14 and the labeling station 32. The control device 38, for example, calculates sales prices on basis of the results of the vision station 12 and the weighing station 14.

Further, a control station 40 can be provided following the labeling station 32. The control station 40 comprises, for example, (at least one) camera 42. With this camera 42, the control station 40 is capable of checking for label presence on food product packages and is also capable of checking for correct label position. Further, with the camera 42 it is possible to check for proper label information on printed labels when the images information of the camera 42 is accordingly analyzed by the control device 38. (For example, the control device 38 uses OCR/OCV.)

The control station 40 can comprise a pusher 43 for removing packaged food products which have been recognized (for example via measuring results of the vision station 12) as not fulfilling certain quality standards.

The vision station 12 comprises a holding device 44 (FIG. 2), which is positioned on the stand 16. For example, the holding device 44 is of the gantry type.

The holding device comprises a bar 46, which is positioned above the tray positioning area 26 at a distance from this tray positioning area 26. The bar 46 holds a first camera 48 and, optionally, a second camera 50. The vision field of the first camera 48 and the second camera 50 is the tray positioning area 26.

The cameras 48 and 50 are, in particular, commercially available cameras.

The cameras 48 and 50 are positioned within the enclosure 24. The holding device 44 can be arranged completely within the enclosure 24 or partially within the enclosure 24 or outside of the enclosure 24.

Within the enclosure 24 light sources 52 for discrete red, green and blue light are arranged. For example, these light sources 52 are light emitting diodes. The enclosure 24 has a reflection area 54 on its walls or at least partially on its walls. For example, a reflection area 54 is formed on a side 56 of the enclosure 24 facing towards the tray positioning area 26 and lying above this tray positioning area 26. For example, the reflection area 54 is formed by panels. The panels are, for example, made from a plastic material.

The light of the light sources 52 is directed towards the reflection area 54 and reflected from there towards the tray positioning area 26. The light of the light sources 52 mixes towards the reflection area 54 and when reflected from the reflection area 54. Such, the tray positioning area 26 is illuminated by white light. In this sense, the reflection area 54 can be seen as a source for white light illuminating the tray positioning area 26. The light sources 52 and the reflection area 54 are formed and arranged in such a way that the tray positioning area 26 is evenly lighted.

It is also possible that instead of "discrete" sources for discrete colors a broadband source or broadband sources for white light are provided. In particular, one or more broadband light emitting diodes are provided. It is in principle also possible that other broadband light sources like halogen lamps can be provided.

On the stand 26, a holding plate 58 is arranged. This holding plate 58 is disposed within the enclosure 24. The conveyor belt 18 is guided over the holding plate 58.

On the holding plate 58 reference fields 60*a*, 60*b*, 60*c*, 60*d* are arranged. The reference field 60*a* is a red color reference field. The reference field 60*b* is a green color reference field and the reference field 60*c* is a blue color reference field. The reference field 60*d* is a white color reference field. The colors of the reference fields correspond to the colors of the light that is emitted by the corresponding light source. Such, the color of the reference field 60*a* corresponds to the color of the light sources emitting red light, the color of the reference field 60*b* corresponds to the color of the green light emitting sources and the color of the reference field 60*c* corresponds to the blue light emitting sources.

The reference field 60d for white color allows balancing on a white target.

The reference fields 60a, 60b, 60c are arranged within the vision range of the first camera 48 (and optionally the second camera 50). In particular, the reference fields 60a, 60b, 60c are arranged at or close to the tray positioning area 26 in such a way that both the reference fields 60a, 60b, 60c and also food product in the tray positioning area 26 is within the vision field of the first camera 48.

Via the reference fields 60a, 60b, 60c, the light level and color balance of the cameras 48, 50 can be monitored. It is possible to adjust camera settings of the cameras 48 and 50 automatically when needed.

The holding device 44 further holds a laser device 62 which is the source of green laser light 64. The laser device 62 generates a (green) laser generated light line 66 (FIG. 7) across the packaged food product. This light line 66 is used for various analysis and evaluation steps that will be described below.

The laser device 62 emits (via a corresponding optic arrangement) a scanning light fan which is oblique to a plane 68 that is perpendicular to the holding plate 58 and the conveyor belt 18. Also, the plane 68 is perpendicular to a transporting direction 70 of food products through the vision station 12. This allows, as described below, a package cover analysis.

A further laser device 63 can be provided for scanning in a line substantially parallel to the transport direction 70. Such a laser device emits a scanning light fan which is indicated in FIG. 2 with the numeral 65. This light fan 65 can be parallel or oblique to a plane perpendicular to the plane 68.

The laser device 63 emits laser light of the same color as the laser device 62.

Further laser devices can be provided emitting scanning light fans.

Figure 4:
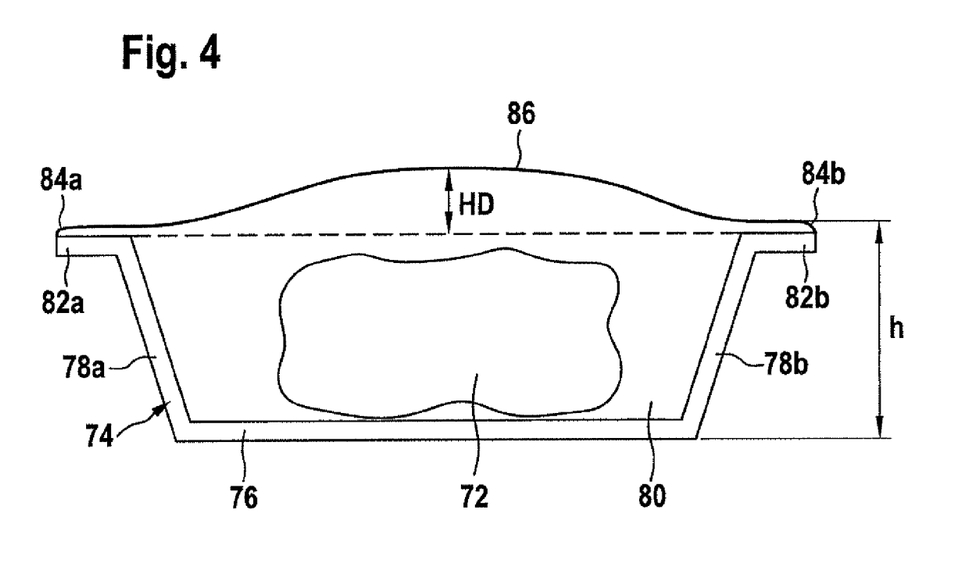
FIG. 4 is a schematic cross section of a sealed tray (tray with cover lid) including a food product.

As indicated in FIG. 4, the food products 72 to be investigated are packaged in respective trays 74. A tray 74 has a base portion 76 and wall portions 78a, 78b. Via the base portion 76 and the wall portions 78a, 78b a reception area 80 for the food product 72 is formed.

The tray 74 further comprises on the wall portions 78a, 78b flange-like extensions 82a, 82b which are parallel to the base portion 76. These extensions 82a, 82b provide seal areas 84a, 84b to which a cover 86 can be attached. The cover 86 is a see-through film-like lid which allows optical access to the food product 72 in the reception area 80.

The seal 86 forms a kind of dome on the tray 74. The cover 86 is formed in such a way that the food product 72 is sealed from the outer atmosphere. Provision can be made that under the cover 86 a protective gas is captured for protection of the food product 72.

It is advantageous when the tray 74 contrasts from the food product contained in the tray. In particular, the tray 74 has a color which is different from red and white when the food product is processed meat. In particular, the tray 74 is of color black.

The food product checking system 10 comprises an evaluation device 88 (FIG. 2) for analyzing pictures taken by the first camera 48 and the optional second camera 50. The evaluation device 88 can be a part of the control device 38 or can be separate from the control device 38 but connected to the control device 38.

The evaluation device 88 receives via corresponding signal lines 90 the pixel data (image data) taken by the cameras 48 and 50. The evaluation device 88 comprises a data storage 92 for storing food product data. By comparing analyzed and evaluated image data with stored data a food product can be identified and/or graded.

Further, the evaluation device 88 comprises a learning section 94 for performing teach-processes to read in data of food products that are not yet stored.

The food product checking system 10 and in particular the vision station 12 functions as follows:

A food product packaged in a tray 74 is positioned in the tray positioning area 26. For the optical analysis of the food product, the tray can be at rest or moving. Such, it is possible to perform a monitoring with the corresponding tray at rest or continuous monitoring.

The light sources 52 produce, respectively, discrete red, green and blue light. The tray positioning area 26 is illuminated with broad spectrum white light from the reception area 80. Glare on a cover 86 can be minimized via reflection of the light from the reception area 80.

Figure 5:
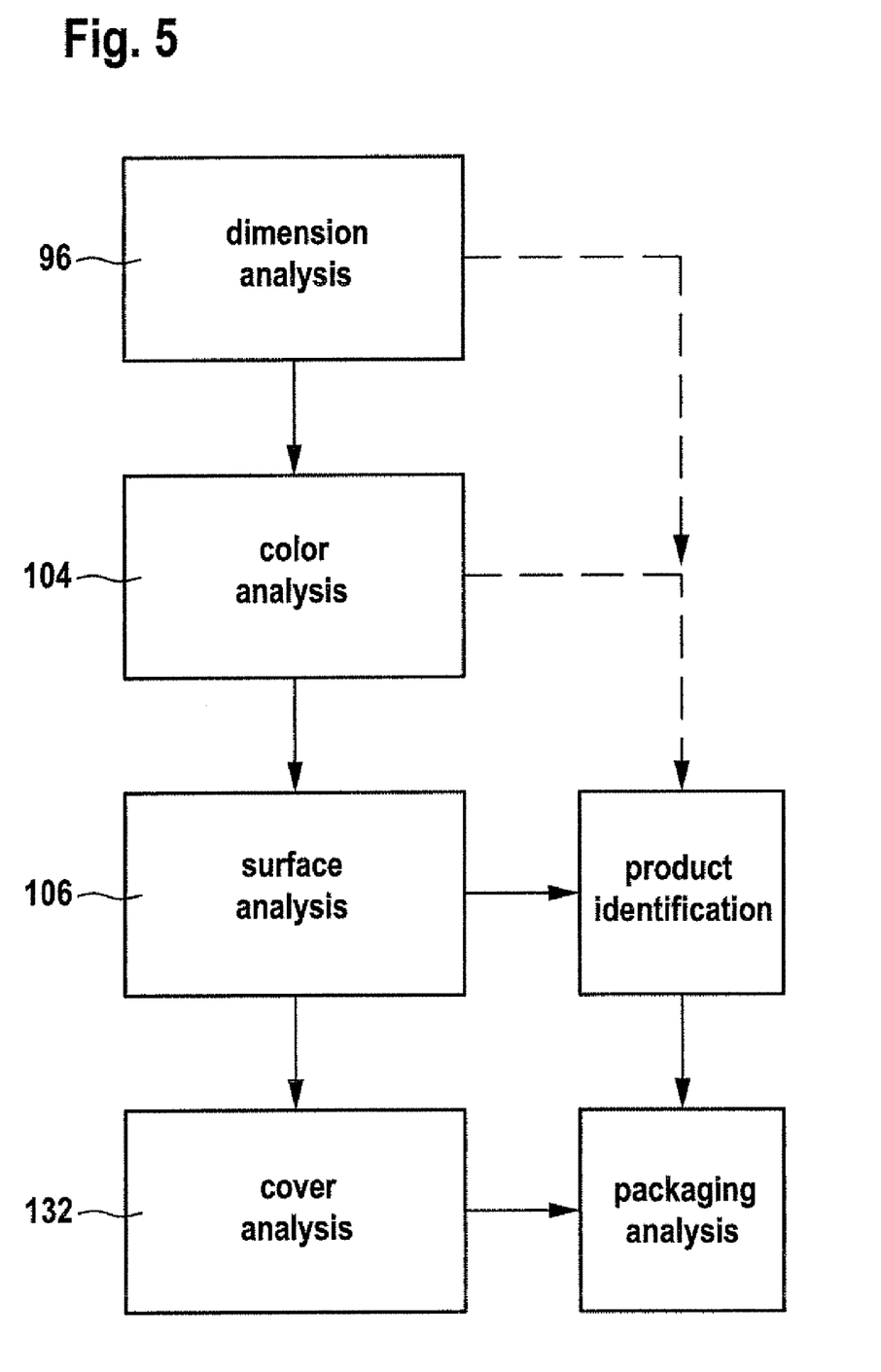
FIG. 5 is a schematic flow chart illustrating an embodiment of food product identification and food product grading.

The camera 48 is triggered on a tray edge. The evaluation device 88 determines the dimensions of the tray. Further, via image processing the contour or shape of the food product 72 in the tray 74 are analyzed. This is indicated in FIG. 5 with the box 96 "dimension analysis".

When the contour/shape of the food product 72 is known, the evaluation device 88 can separate (in an image) the food product 72 from the tray 74.

Figure 7:
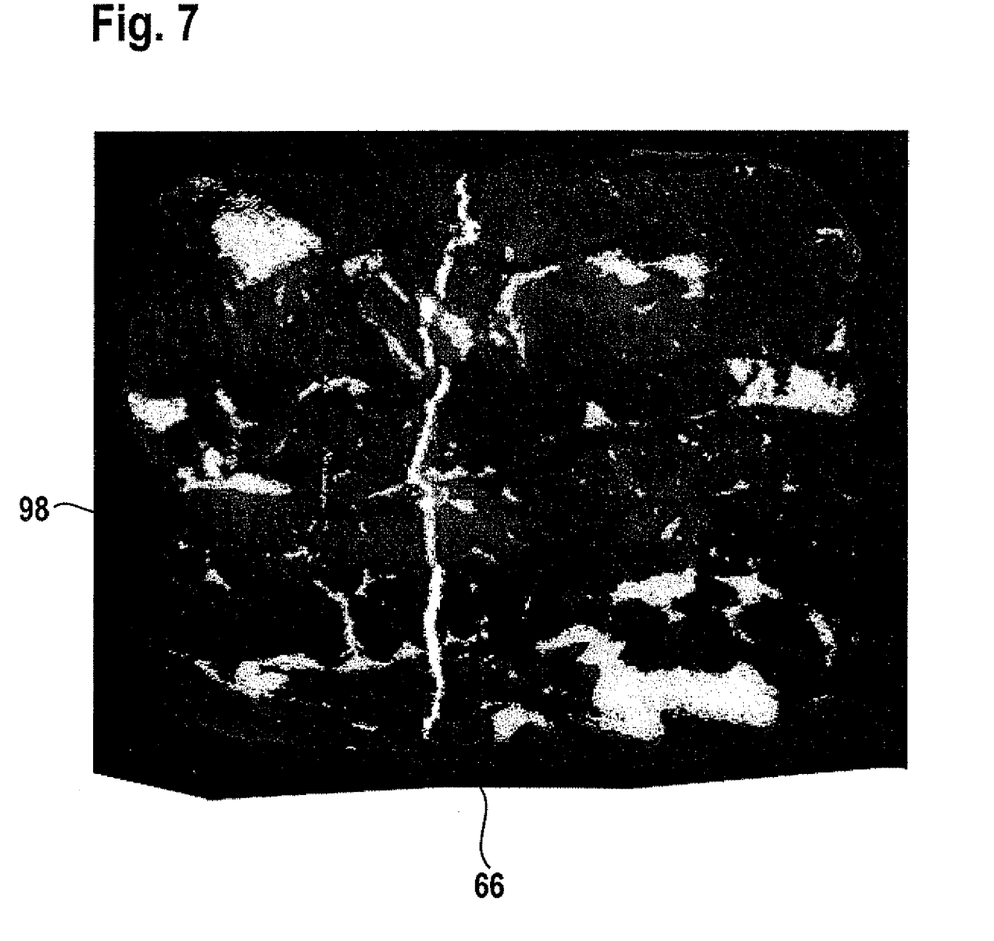
FIG. 7 shows an image of packaged meat during an analyzing step; the original image has blue, red and green areas. It is possible to distinguish between lean areas, fat areas and laser generated light areas.

FIG. 7 shows an image example of a food product 98 (meat) that is generated by the evaluation device 88 after separating the food product 98 from the tray 74.

The laser generated light line 66 is produced across the food product 72 and also on the extensions 82a, 82b on the tray 74. The evaluation device 88 searches for the corresponding portion 100a, 100b of the light lines 66 on the extensions 82a, 82b. Further, the evaluation device 88 evaluates the light line 102 outside the tray 74. The light line on the reference fields 60a, 60b, 60c is, for example, evaluated.

Between the light line 102 and the portion 100a, 100b there is an offset $d_1$, $d_2$ depending on the height h (FIG. 4) of the tray 74. The larger this offset, the higher the tray 74. FIG. 3 shows two examples: A small offset $d_1$ and a larger offset $d_2$. The corresponding trays have different heights, whereas the tray responsible for the offset $d_2$ has a larger height than the other tray. The evaluation device 88 can determine the offset $d_1$, $d_2$ via imaging processing. From this offset, the height of the tray can be determined.

Figure 6:
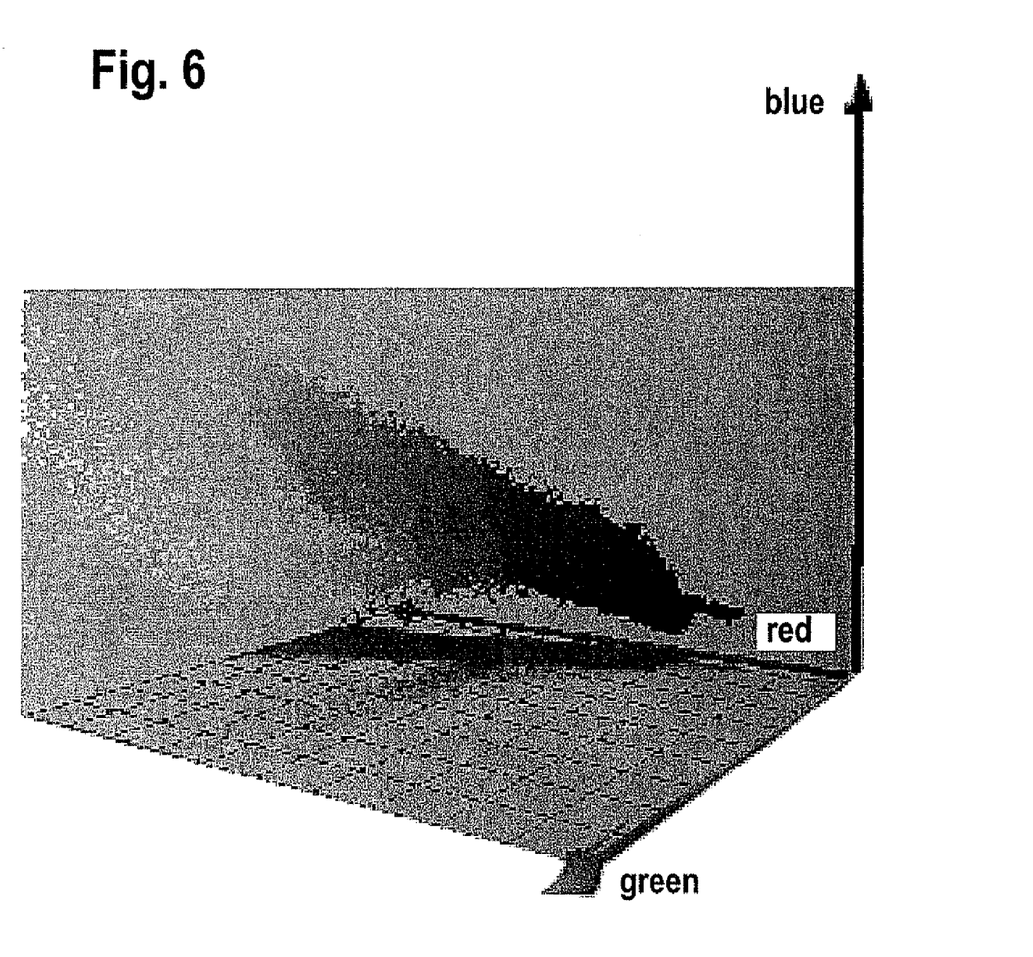
FIG. 6 is a schematic diagram for illustrating a color analysis; the diagram has as axes the colors red, green and blue and an analyzed food product is pictured as points.

The evaluation device 88 performs a color analysis of images provided by the first camera 48. This is indicated in FIG. 5 with the box 104. For the color analysis, the pixels of the images provided by the first camera 48 are grouped in a red, green, blue color space as indicated in FIG. 6. With a color analysis, different areas in the food product can be distinguished. For example, if the food product is meat, bone areas, lean areas and fat areas can be distinguished. Further, with the color analysis it is possible to distinguish a laser light area for the laser generated light line 66. This area is used for further analysis.

FIG. 7 shows a picture of meat following a color analysis. The original picture is a false-colored blue picture including blue areas and red areas and also a green area for the laser generated light line 66. The image is segmented and allows to distinguish between lean areas and fat areas.

Further, a surface analysis is performed as indicated in FIG. 5 via the box 106. The surface analysis uses the laser generated light line 66.

The evaluation device 88 further analyzes the laser generated light line 66 on the food product 72. For this, the corresponding green pixels in taken images are evaluated.

As indicated in FIGS. 8(a) to 8(e), the light line 66 can be segmented depending on the food product.

Figure 8:
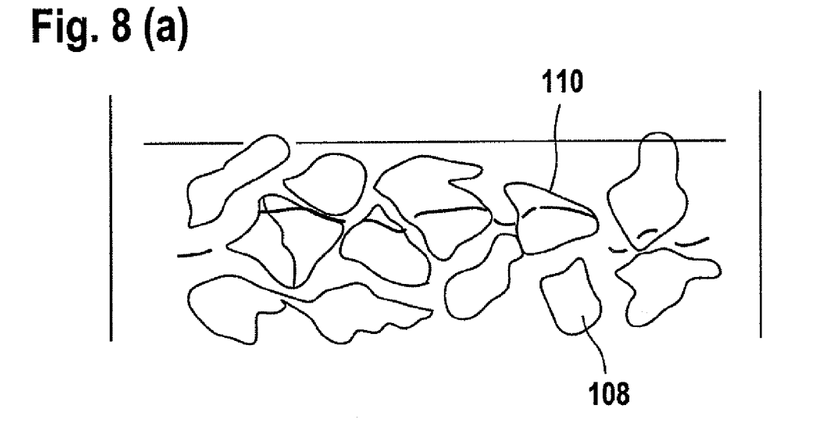
FIGS. 8(a) to (e) show different samples of food products and a laser generated light line.

For example, as indicated in FIG. 8(a), when the food product (for example, meat) is stew meat 108, then the corresponding laser line 110 is fragmented. Between different parts of the stew meat there are offsets.

If, as indicated in FIG. 8(b), the food product is multiple meat cut 112, the corresponding light line 114 is less fragmented but can have larger offsets between neighboring cut portions.

If the food product is a single slice 116, as indicated in FIG. 8(c), the corresponding light line 118 is not fragmented.

Also, via analysis of the light line it is possible to distinguish whether the food product comprises thick slices or thin slices. FIG. 8(d) shows rather thin slices 120. The light line 122 has offsets 124 indicating different slices. For small slices 120, the offsets are smaller than for thicker slices 126, as indicated in FIG. 8(e). There, the corresponding light line 128 has offsets 130 at the transition between different slices Also, the light line 128 is less segmented than the light line 122 indicating that less slices are provided.

Using the color information from the color analysis and the surface analysis information, food products can be identified and/or graded.

It is also possible to perform a cover analysis, as indicated with the box 132 in FIG. 5. The cover analysis is, for example, performed before the color analysis or after the surface analysis.

Figure 9:
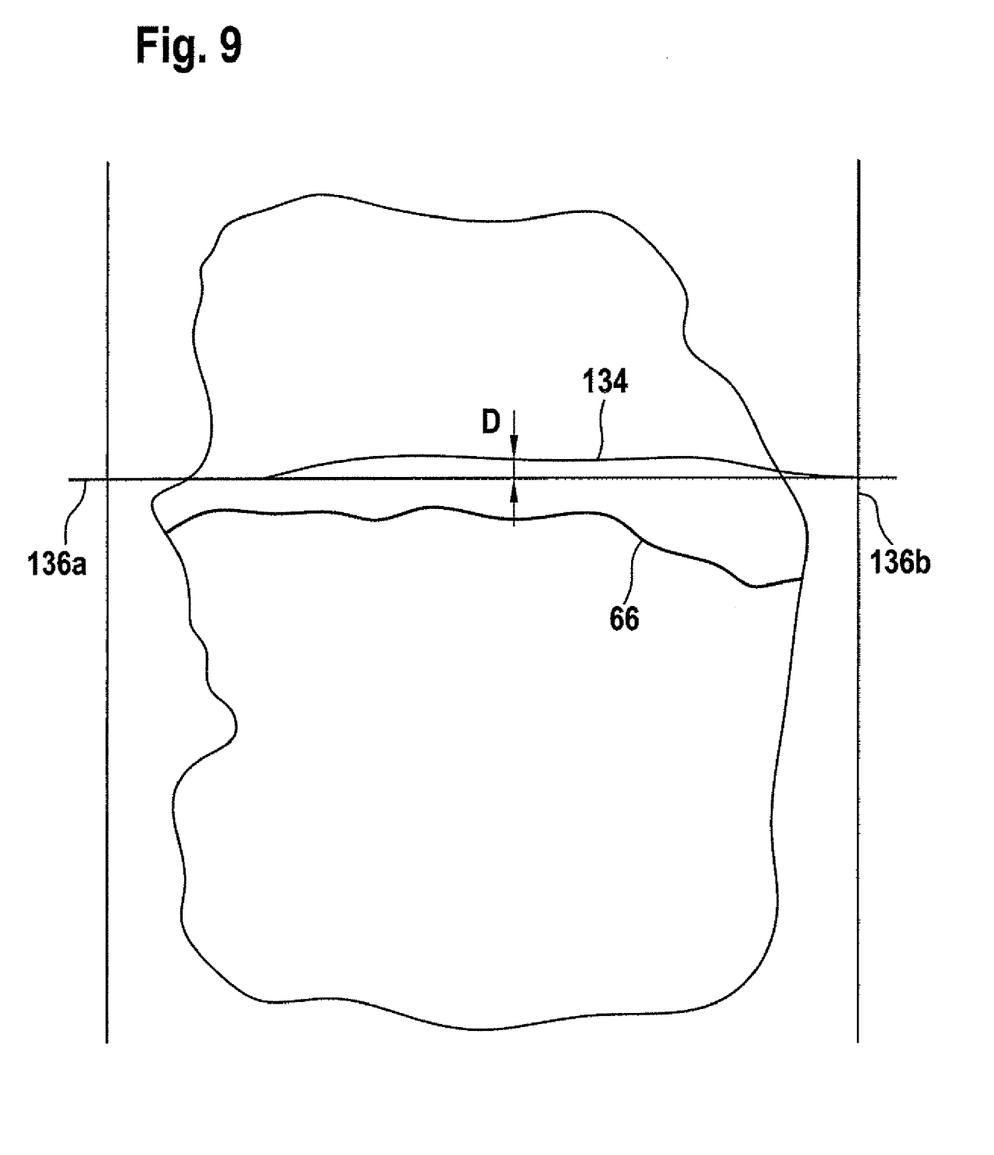
FIG. 9 shows schematically a food product and different laser generated light lines allowing a packaging analysis.

A film-like cover 86 is responsible for a further laser generated light line 134 (FIG. 9). This light line 134 is brought about by laser light reflection on the cover 86. By comparing an offset D (FIG. 9) between the light line 134 and light line portions 136a, 136b on the extensions 82a, 82b of the tray 74, it is possible to determine the height of the film dome as indicated with HD in FIG. 4. Such, it is possible to determine whether the cover 86 touches the food product or not, for example, it is also possible to compare the position of a film dome (as detected by the light line 134) to the position of the product in its package. If the two positions coincide, the product is touched by the cover 86.

Also, when analyzing the light line portions 136a, 136b on the extensions 82a, 82b it is possible to determine whether intruding material is in the seal areas 84a, 84b. For example, food product parts can be between the cover 86 and the extensions 82a, 82b. The evaluation device 88 analyzes via imaging processing whether the seal areas 84a, 84b have the tray color (for example, black). If another color than the tray color is found there, there must be something in a seal area under or in the cover 86.

As mentioned above, the packaging analysis via the cover analysis can be performed before the color analysis.

In a particular embodiment, the checking procedure for food products to identify the food products and grade the food products is performed as following:

The first camera 48 is triggered on a tray edge of a tray 74. The evaluation device 88 searches for the light line portions on both extensions 82a, 82b in order to calculate the tray height H. Afterwards, light line 134 of the cover 86 is searched for (via image processing in the evaluation device 88 using the pixel data provided by the first camera 48). Using the corresponding information, the height HD of the cover dome is calculated.

Further, the parameter of the tray 74, that is the extensions 82a, 82b are inspected with regard to intrusions like food product material. This is done by looking for color pixels which should not be there without an intrusion.

The evaluation device 88 then determines the contour or shape of the food product 82 and segments the food product into areas which are distinguished by their color. In particular, the image of the food product 72 is segmented into laser areas and lean and fat areas.

The image of the food product 72 within its contours is analyzed using different analysis modules. The analysis results in a numeric output for each analysis module. In a particular example, ten to fifteen (or more) different analysis modules are performed. Examples for analysis modules are:

The texture of the food product around a laser generated light line 66. (With such an analysis, it is for example possible to differentiate cut meat from cubed meat.) Further examples of analysis modules are the number of light line segments, the length distribution of light line segments, the angle distribution of light line segments or the offset between light line segments. Further, the shape of the food product outline is analyzed. This could give several criteria. Also, the distribution of size of fat blobs is analyzed. This can be done by image quadrant. Another criteria is the distribution of shape of the fat blobs. This can also be done by image quadrant.

The output values calculated by the evaluation device 88 are used for eliminating non-matching food products. The corresponding data of the food products are stored in the data storage 92. If a matching product identification is reached, the corresponding information is provided via the control device 38 to the labeling device 36.

In an embodiment in accordance with the present invention, non-matching food products are eliminated until one matching food product is left.

The second camera 50, which is optional, is for making a partial scan of only the laser generated light line area during food product traveled through the vision station 12. For example, the second camera 50 provides image data for determining whether the cover 86 touches the food product. The evaluation device 88 can then give a corresponding signal which effects in ignoring the corresponding tray for labeling at the labeling station 32 and for rejecting the corresponding package at the discharge.

The second camera 50 also monitors the reference fields 60a, 60b, 60c. The learning module 94 can be an intelligent learning module or a setup module. When feeding a new product through the vision station 12, the corresponding output values for each of the modules mentioned above are calculated. The learning module 94 can check whether the corresponding food product overlaps with stored food product data or indicates that the new product is unique. Also, range settings for each criterion can be suggested.

The invention claimed is:

1. A food product checking system for at least one of identification and grading of food products packed in a tray, wherein the tray is sealed by a see-through lid comprising:
    a tray positioning area;
    an illumination device for illuminating the food product with white light;
    at least one camera for taking images of the illuminated food product;
    at least one evaluation device for image processing of taken images;
    wherein the evaluation device is adapted to perform a color analysis of taken images; and
    a laser device which is adapted to produce at least one laser generated light line across the tray.

2. The food product checking system in accordance with claim 1, wherein the white light is a superposition of red light, green light and blue light.

3. The food product checking system in accordance with claim 1, wherein the illumination device comprises a source for white light.

4. The food product checking system in accordance with claim 1, wherein the illumination device comprises sources for red, green and blue light.

5. The food product checking system in accordance with claim 1, comprising a reflection area from which white light is directed towards the tray positioning area.

6. The food product checking system in accordance with claim 4, wherein the light of the sources for red, green and blue light is directed towards a reflection area.

7. The food product checking system in accordance with claim 1, wherein at least one light emitting diode is provided as a light source.

8. The food product checking system in accordance with claim 1, wherein an enclosure is provided for the tray positioning area.

9. The food product checking system in accordance with claim 8, wherein the enclosure has openings allowing a through-put of trays.

10. The food product checking system in accordance with claim 1, wherein color reference fields are arranged within the vision range of the at least one camera.

11. The food product checking system in accordance with claim 10, wherein at least one color reference field for each of the colors red, green and blue is provided.

12. The food product checking system in accordance with claim 10, wherein the color reference fields are arranged at or close to the tray positioning area.

13. The food product checking system in accordance with claim 1, wherein at least one color reference field for the color white is provided.

14. The food product checking system in accordance with claim 1, wherein the evaluation device is adapted to analyze an image with regard to the positions of the colors red, green and blue.

15. The food product checking system in accordance with claim 1, wherein the food product is meat or sausage and the evaluation device is adapted to distinguish at least one of fat areas, lean areas and bone areas in the meat or the sausage.

16. The food product checking system in accordance with claim 1, wherein the evaluation device is adapted to identify the contour or shape of the food product in the tray and separate the food product from the tray.

17. The food product checking system in accordance with claim 1, wherein the laser device emits light in an angle with regard to a plane perpendicular to the tray positioning area.

18. The food product checking system in accordance with claim 1, wherein the laser device generates green light.

19. The food product checking system in accordance with claim 1, wherein the evaluation device is adapted to recognize laser generated light lines in a taken image.

20. The food product checking system in accordance with claim 1, wherein the evaluation device is adapted to analyze laser generated light lines in images.

21. The food product checking system in accordance with claim 20, wherein the evaluation device is adapted to analyze a laser generated light line with regard to segmentation.

22. The food product checking system in accordance with claim 21, wherein the evaluation device is adapted to analyze a laser generated light line with regard to at least one of number of segments, length of segments, length distribution of segments, angle of segments, angle distribution of segments and offset between segments.

23. The food product checking system in accordance with claim 19, wherein the evaluation device is adapted to analyze the texture of the food product around a laser generated light line.

24. The food product checking system in accordance with claim 1, wherein the evaluation device is adapted to analyze at least one of shape of the food product, shape of areas of the food product, distribution of shape of areas of the food product, size of areas of the food product, and distribution of size of areas of the food product.

25. The food product checking system in accordance with claim 1, wherein the evaluation device evaluates a laser generated light line caused by light reflection of said lid.

26. The food product checking system in accordance with claim 25, wherein the evaluation device is adapted to determine a dome height of the lid by comparing the reflection light line of the lid with the light reflected on a tray edge.

27. The food product checking system in accordance with claim 1, wherein the evaluation device is adapted to analyze the height of the tray by comparing the offset of light reflected from the tray positioning area or an area close to the tray positioning area to a laser generated light area on the tray.

28. The food product checking system in accordance with claim 1, wherein the evaluation device is adapted to analyze a tray seal area with regard to inclusions.

29. The food product checking system in accordance with claim 1, comprising a first camera and at least one further camera for scanning a laser generated light area.

30. The food product checking system in accordance with claim 1, comprising a conveyor for transporting trays.

31. The food product checking system in accordance with claim 1, wherein the evaluation device comprises a data storage for storing at least one of product identification and product grading data.

32. The food product checking system in accordance with claim 1, wherein the evaluation device comprises a learning section for new products.

33. A method for identifying or grading food products packaged in a tray, wherein the tray is sealed by a see-through lid comprising:
   evaluating the shape of the food product in the tray; and
   analyzing the food product with regard to different areas in the food product;
   wherein for analyzing the food product multiple analysis modules are performed based on different analysis criteria, each analysis module providing an output;
   wherein said outputs are compared to stored food product data; and
   wherein at least one laser generated light line across the tray is produced.

34. The method in accordance with claim 33, wherein said outputs are numerical values.

35. The method in accordance with claim 33, wherein the analysis comprises a color analysis of the food product and a surface analysis of the food product.

36. The method in accordance with claim 33, wherein the analysis is based on optical data.

37. The method in accordance with claim 33, wherein the analysis is based on image data processing of images taken by at least one camera.

* * * * *